US012617078B2

(12) United States Patent
  Heiliger

(10) Patent No.: US 12,617,078 B2
(45) Date of Patent: May 5, 2026

(54) ROBOTIC SURGICAL ASSEMBLIES INCLUDING SURGICAL INSTRUMENTS HAVING ARTICULATABLE WRIST ASSEMBLIES

(71) Applicant: Covidien LP, Mansfield, MA (US)

(72) Inventor: Zachary S. Heiliger, Lafayette, CO (US)

(73) Assignee: Covidien LP, Mansfield, MA (US)

( * ) Notice: Subject to any disclaimer, the term of this patent is extended or adjusted under 35 U.S.C. 154(b) by 385 days.

(21) Appl. No.: 18/206,360

(22) Filed: Jun. 6, 2023

(65) Prior Publication Data

US 2023/0405804 A1      Dec. 21, 2023

Related U.S. Application Data

(60) Provisional application No. 63/352,302, filed on Jun. 15, 2022.

(51) Int. Cl.
  B25J 9/08       (2006.01)
  A61B 34/30      (2016.01)

(52) U.S. Cl.
  CPC ................. B25J 9/08 (2013.01); A61B 34/30 (2016.02); A61B 2034/305 (2016.02)

(58) Field of Classification Search
  CPC .... A61B 34/71; A61B 34/30; A61B 2034/305
  See application file for complete search history.

(56) References Cited

U.S. PATENT DOCUMENTS

| | | | |
|---|---|---|---|
| 6,132,368 | A | 10/2000 | Cooper |
| 6,206,903 | B1 | 3/2001 | Ramans |
| 6,246,200 | B1 | 6/2001 | Blumenkranz et al. |
| 6,312,435 | B1 | 11/2001 | Wallace et al. |
| 6,331,181 | B1 | 12/2001 | Tierney et al. |
| 6,394,998 | B1 | 5/2002 | Wallace et al. |
| 6,424,885 | B1 | 7/2002 | Niemeyer et al. |
| 6,441,577 | B2 | 8/2002 | Blumenkranz et al. |
| 6,459,926 | B1 | 10/2002 | Nowlin et al. |
| 6,491,691 | B1 | 12/2002 | Morley et al. |
| 6,491,701 | B2 | 12/2002 | Tierney et al. |
| 6,493,608 | B1 | 12/2002 | Niemeyer |
| 6,565,554 | B1 | 5/2003 | Niemeyer |
| 6,645,196 | B1 | 11/2003 | Nixon et al. |
| 6,659,939 | B2 | 12/2003 | Moll |
| 6,671,581 | B2 | 12/2003 | Niemeyer et al. |
| 6,676,684 | B1 | 1/2004 | Morley et al. |

(Continued)

FOREIGN PATENT DOCUMENTS

| | | |
|---|---|---|
| CN | 106361475 A | 2/2017 |
| CN | 106672105 A | 5/2017 |

(Continued)

*Primary Examiner* — Carl H Layno
*Assistant Examiner* — Bryan Mcallister Lee
(74) *Attorney, Agent, or Firm* — Carter, DeLuca & Farrell, LLP

(57)                ABSTRACT

A surgical instrument for use in a robotic surgical system includes an end effector, a housing configured to be operably coupled to an instrument drive unit, a shaft extending distally from the housing, a tensegrity wrist assembly movably coupling the end effector to a distal end portion of the shaft, and articulation cables that adjust the pitch and yaw of the end effector relative to the shaft.

20 Claims, 8 Drawing Sheets

(56) References Cited

U.S. PATENT DOCUMENTS

| | | | |
|---|---|---|---|
| 6,685,698 B2 | 2/2004 | Morley et al. |
| 6,699,235 B2 | 3/2004 | Wallace et al. |
| 6,714,839 B2 | 3/2004 | Salisbury, Jr. et al. |
| 6,716,233 B1 | 4/2004 | Whitman |
| 6,728,599 B2 | 4/2004 | Wang et al. |
| 6,746,443 B1 | 6/2004 | Morley et al. |
| 6,766,204 B2 | 7/2004 | Niemeyer et al. |
| 6,770,081 B1 | 8/2004 | Cooper et al. |
| 6,772,053 B2 | 8/2004 | Niemeyer |
| 6,783,524 B2 | 8/2004 | Anderson et al. |
| 6,793,652 B1 | 9/2004 | Whitman et al. |
| 6,793,653 B2 | 9/2004 | Sanchez et al. |
| 6,799,065 B1 | 9/2004 | Niemeyer |
| 6,837,883 B2 | 1/2005 | Moll et al. |
| 6,839,612 B2 | 1/2005 | Sanchez et al. |
| 6,840,938 B1 | 1/2005 | Morley et al. |
| 6,843,403 B2 | 1/2005 | Whitman |
| 6,846,309 B2 | 1/2005 | Whitman et al. |
| 6,866,671 B2 | 3/2005 | Tierney et al. |
| 6,871,117 B2 | 3/2005 | Wang et al. |
| 6,879,880 B2 | 4/2005 | Nowlin et al. |
| 6,899,705 B2 | 5/2005 | Niemeyer |
| 6,902,560 B1 | 6/2005 | Morley et al. |
| 6,936,042 B2 | 8/2005 | Wallace et al. |
| 6,951,535 B2 | 10/2005 | Ghodoussi et al. |
| 6,974,449 B2 | 12/2005 | Niemeyer |
| 6,991,627 B2 | 1/2006 | Madhani et al. |
| 6,994,708 B2 | 2/2006 | Manzo |
| 7,048,745 B2 | 5/2006 | Tierney et al. |
| 7,066,926 B2 | 6/2006 | Wallace et al. |
| 7,118,582 B1 | 10/2006 | Wang et al. |
| 7,125,403 B2 | 10/2006 | Julian et al. |
| 7,155,315 B2 | 12/2006 | Niemeyer et al. |
| 7,239,940 B2 | 7/2007 | Wang et al. |
| 7,306,597 B2 | 12/2007 | Manzo |
| 7,357,774 B2 | 4/2008 | Cooper |
| 7,373,219 B2 | 5/2008 | Nowlin et al. |
| 7,379,790 B2 | 5/2008 | Toth et al. |
| 7,386,365 B2 | 6/2008 | Nixon |
| 7,391,173 B2 | 6/2008 | Schena |
| 7,398,707 B2 | 7/2008 | Morley et al. |
| 7,413,565 B2 | 8/2008 | Wang et al. |
| 7,453,227 B2 | 11/2008 | Prisco et al. |
| 7,524,320 B2 | 4/2009 | Tierney et al. |
| 7,574,250 B2 | 8/2009 | Niemeyer |
| 7,594,912 B2 | 9/2009 | Cooper et al. |
| 7,607,440 B2 | 10/2009 | Coste-Maniere et al. |
| 7,666,191 B2 | 2/2010 | Orban, III et al. |
| 7,682,357 B2 | 3/2010 | Ghodoussi et al. |
| 7,689,320 B2 | 3/2010 | Prisco et al. |
| 7,695,481 B2 | 4/2010 | Wang et al. |
| 7,695,485 B2 | 4/2010 | Whitman et al. |
| 7,699,855 B2 | 4/2010 | Anderson et al. |
| 7,713,263 B2 | 5/2010 | Niemeyer |
| 7,725,214 B2 | 5/2010 | Diolaiti |
| 7,727,244 B2 | 6/2010 | Orban, III et al. |
| 7,741,802 B2 | 6/2010 | Prisco |
| 7,756,036 B2 | 7/2010 | Druke et al. |
| 7,757,028 B2 | 7/2010 | Druke et al. |
| 7,762,825 B2 | 7/2010 | Burbank et al. |
| 7,778,733 B2 | 8/2010 | Nowlin et al. |
| 7,803,151 B2 | 9/2010 | Whitman |
| 7,806,891 B2 | 10/2010 | Nowlin et al. |
| 7,819,859 B2 | 10/2010 | Prisco et al. |
| 7,819,885 B2 | 10/2010 | Cooper |
| 7,824,401 B2 | 11/2010 | Manzo et al. |
| 7,835,823 B2 | 11/2010 | Sillman et al. |
| 7,843,158 B2 | 11/2010 | Prisco |
| 7,865,266 B2 | 1/2011 | Moll et al. |
| 7,865,269 B2 | 1/2011 | Prisco et al. |
| 7,886,743 B2 | 2/2011 | Cooper et al. |
| 7,899,578 B2 | 3/2011 | Prisco et al. |
| 7,907,166 B2 | 3/2011 | Lamprecht et al. |
| 7,935,130 B2 | 5/2011 | Williams |
| 7,963,913 B2 | 6/2011 | Devengenzo et al. |
| 7,983,793 B2 | 7/2011 | Toth et al. |
| 8,002,767 B2 | 8/2011 | Sanchez |
| 8,004,229 B2 | 8/2011 | Nowlin et al. |
| 8,012,170 B2 | 9/2011 | Whitman et al. |
| 8,054,752 B2 | 11/2011 | Druke et al. |
| 8,062,288 B2 | 11/2011 | Cooper et al. |
| 8,079,950 B2 | 12/2011 | Stern et al. |
| 8,100,133 B2 | 1/2012 | Mintz et al. |
| 8,108,072 B2 | 1/2012 | Zhao et al. |
| 8,120,301 B2 | 2/2012 | Goldberg et al. |
| 8,142,447 B2 | 3/2012 | Cooper et al. |
| 8,147,503 B2 | 4/2012 | Zhao et al. |
| 8,151,661 B2 | 4/2012 | Schena et al. |
| 8,155,479 B2 | 4/2012 | Hoffman et al. |
| 8,182,469 B2 | 5/2012 | Anderson et al. |
| 8,202,278 B2 | 6/2012 | Orban, III et al. |
| 8,206,406 B2 | 6/2012 | Orban, III |
| 8,210,413 B2 | 7/2012 | Whitman et al. |
| 8,216,250 B2 | 7/2012 | Orban, III et al. |
| 8,220,468 B2 | 7/2012 | Cooper et al. |
| 8,256,319 B2 | 9/2012 | Cooper et al. |
| 8,285,517 B2 | 10/2012 | Sillman et al. |
| 8,315,720 B2 | 11/2012 | Mohr et al. |
| 8,335,590 B2 | 12/2012 | Costa et al. |
| 8,347,757 B2 | 1/2013 | Duval |
| 8,374,723 B2 | 2/2013 | Zhao et al. |
| 8,418,073 B2 | 4/2013 | Mohr et al. |
| 8,419,717 B2 | 4/2013 | Diolaiti et al. |
| 8,423,182 B2 | 4/2013 | Robinson et al. |
| 8,452,447 B2 | 5/2013 | Nixon |
| 8,454,585 B2 | 6/2013 | Whitman |
| 8,499,992 B2 | 8/2013 | Whitman et al. |
| 8,508,173 B2 | 8/2013 | Goldberg et al. |
| 8,528,440 B2 | 9/2013 | Morley et al. |
| 8,529,582 B2 | 9/2013 | Devengenzo et al. |
| 8,540,748 B2 | 9/2013 | Murphy et al. |
| 8,551,116 B2 | 10/2013 | Julian et al. |
| 8,562,594 B2 | 10/2013 | Cooper et al. |
| 8,594,841 B2 | 11/2013 | Zhao et al. |
| 8,597,182 B2 | 12/2013 | Stein et al. |
| 8,597,280 B2 | 12/2013 | Cooper et al. |
| 8,600,551 B2 | 12/2013 | Itkowitz et al. |
| 8,608,773 B2 | 12/2013 | Tierney et al. |
| 8,620,473 B2 | 12/2013 | Diolaiti et al. |
| 8,624,537 B2 | 1/2014 | Nowlin et al. |
| 8,634,957 B2 | 1/2014 | Toth et al. |
| 8,638,056 B2 | 1/2014 | Goldberg et al. |
| 8,638,057 B2 | 1/2014 | Goldberg et al. |
| 8,644,988 B2 | 2/2014 | Prisco et al. |
| 8,666,544 B2 | 3/2014 | Moll et al. |
| 8,668,638 B2 | 3/2014 | Donhowe et al. |
| 8,746,252 B2 | 6/2014 | McGrogan et al. |
| 8,749,189 B2 | 6/2014 | Nowlin et al. |
| 8,749,190 B2 | 6/2014 | Nowlin et al. |
| 8,758,352 B2 | 6/2014 | Cooper et al. |
| 8,761,930 B2 | 6/2014 | Nixon |
| 8,768,516 B2 | 7/2014 | Diolaiti et al. |
| 8,786,241 B2 | 7/2014 | Nowlin et al. |
| 8,790,243 B2 | 7/2014 | Cooper et al. |
| 8,808,164 B2 | 8/2014 | Hoffman et al. |
| 8,816,628 B2 | 8/2014 | Nowlin et al. |
| 8,821,480 B2 | 9/2014 | Burbank |
| 8,821,589 B2 | 9/2014 | Rifkin |
| 8,823,308 B2 | 9/2014 | Nowlin et al. |
| 8,827,989 B2 | 9/2014 | Niemeyer |
| 8,838,270 B2 | 9/2014 | Druke et al. |
| 8,852,174 B2 | 10/2014 | Burbank |
| 8,858,547 B2 | 10/2014 | Brogna |
| 8,862,268 B2 | 10/2014 | Robinson et al. |
| 8,864,751 B2 | 10/2014 | Prisco et al. |
| 8,864,752 B2 | 10/2014 | Diolaiti et al. |
| 8,903,546 B2 | 12/2014 | Diolaiti et al. |
| 8,903,549 B2 | 12/2014 | Itkowitz et al. |
| 8,911,428 B2 | 12/2014 | Cooper et al. |
| 8,912,746 B2 | 12/2014 | Reid et al. |
| 8,944,070 B2 | 2/2015 | Guthart |
| 8,989,903 B2 | 3/2015 | Weir et al. |
| 9,002,518 B2 | 4/2015 | Manzo |
| 9,014,856 B2 | 4/2015 | Manzo et al. |

(56)        References Cited

U.S. PATENT DOCUMENTS

| | | | |
|---|---|---|---|
| 9,016,540 | B2 | 4/2015 | Whitman et al. |
| 9,019,345 | B2 | 4/2015 | O'Grady et al. |
| 9,043,027 | B2 | 5/2015 | Durant et al. |
| 9,050,120 | B2 | 6/2015 | Swarup et al. |
| 9,055,961 | B2 | 6/2015 | Manzo et al. |
| 9,068,628 | B2 | 6/2015 | Solomon et al. |
| 9,078,684 | B2 | 7/2015 | Williams |
| 9,084,623 | B2 | 7/2015 | Gomez et al. |
| 9,095,362 | B2 | 8/2015 | Dachs, II et al. |
| 9,096,033 | B2 | 8/2015 | Holop et al. |
| 9,101,381 | B2 | 8/2015 | Burbank et al. |
| 9,113,877 | B1 | 8/2015 | Whitman et al. |
| 9,138,284 | B2 | 9/2015 | Krom et al. |
| 9,144,456 | B2 | 9/2015 | Rosa et al. |
| 9,198,730 | B2 | 12/2015 | Prisco et al. |
| 9,204,923 | B2 | 12/2015 | Manzo et al. |
| 9,226,648 | B2 | 1/2016 | Saadat et al. |
| 9,226,750 | B2 | 1/2016 | Weir et al. |
| 9,226,761 | B2 | 1/2016 | Burbank |
| 9,232,984 | B2 | 1/2016 | Guthart et al. |
| 9,241,766 | B2 | 1/2016 | Duque et al. |
| 9,241,767 | B2 | 1/2016 | Prisco et al. |
| 9,241,769 | B2 | 1/2016 | Larkin et al. |
| 9,259,275 | B2 | 2/2016 | Burbank |
| 9,259,277 | B2 | 2/2016 | Rogers et al. |
| 9,259,281 | B2 | 2/2016 | Griffiths et al. |
| 9,259,282 | B2 | 2/2016 | Azizian et al. |
| 9,261,172 | B2 | 2/2016 | Solomon et al. |
| 9,265,567 | B2 | 2/2016 | Orban, III et al. |
| 9,265,584 | B2 | 2/2016 | Itkowitz et al. |
| 9,283,049 | B2 | 3/2016 | Diolaiti et al. |
| 9,301,811 | B2 | 4/2016 | Goldberg et al. |
| 9,314,307 | B2 | 4/2016 | Richmond et al. |
| 9,317,651 | B2 | 4/2016 | Nixon |
| 9,345,546 | B2 | 5/2016 | Toth et al. |
| 9,393,017 | B2 | 7/2016 | Flanagan et al. |
| 9,402,689 | B2 | 8/2016 | Prisco et al. |
| 9,417,621 | B2 | 8/2016 | Diolaiti |
| 9,424,303 | B2 | 8/2016 | Hoffman et al. |
| 9,433,418 | B2 | 9/2016 | Whitman et al. |
| 9,446,517 | B2 | 9/2016 | Burns et al. |
| 9,452,020 | B2 | 9/2016 | Griffiths et al. |
| 9,474,569 | B2 | 10/2016 | Manzo et al. |
| 9,480,533 | B2 | 11/2016 | Devengenzo et al. |
| 9,503,713 | B2 | 11/2016 | Zhao et al. |
| 9,550,300 | B2 | 1/2017 | Danitz et al. |
| 9,554,859 | B2 | 1/2017 | Nowlin et al. |
| 9,566,124 | B2 | 2/2017 | Prisco et al. |
| 9,579,164 | B2 | 2/2017 | Itkowitz et al. |
| 9,585,641 | B2 | 3/2017 | Cooper et al. |
| 9,615,883 | B2 | 4/2017 | Schena et al. |
| 9,623,563 | B2 | 4/2017 | Nixon |
| 9,623,902 | B2 | 4/2017 | Griffiths et al. |
| 9,629,520 | B2 | 4/2017 | Diolaiti |
| 9,662,177 | B2 | 5/2017 | Weir et al. |
| 9,664,262 | B2 | 5/2017 | Donlon et al. |
| 9,675,354 | B2 | 6/2017 | Weir et al. |
| 9,687,312 | B2 | 6/2017 | Dachs, II et al. |
| 9,700,334 | B2 | 7/2017 | Hinman et al. |
| 9,718,190 | B2 | 8/2017 | Larkin et al. |
| 9,730,719 | B2 | 8/2017 | Brisson et al. |
| 9,737,199 | B2 | 8/2017 | Pistor et al. |
| 9,784,249 | B2 | 10/2017 | Li et al. |
| 9,795,446 | B2 | 10/2017 | DiMaio et al. |
| 9,797,484 | B2 | 10/2017 | Solomon et al. |
| 9,801,690 | B2 | 10/2017 | Larkin et al. |
| 9,814,530 | B2 | 11/2017 | Weir et al. |
| 9,814,536 | B2 | 11/2017 | Goldberg et al. |
| 9,814,537 | B2 | 11/2017 | Itkowitz et al. |
| 9,820,823 | B2 | 11/2017 | Richmond et al. |
| 9,827,059 | B2 | 11/2017 | Robinson et al. |
| 9,830,371 | B2 | 11/2017 | Hoffman et al. |
| 9,839,481 | B2 | 12/2017 | Blumenkranz et al. |
| 9,839,487 | B2 | 12/2017 | Dachs, II |
| 9,850,994 | B2 | 12/2017 | Schena |
| 9,855,102 | B2 | 1/2018 | Blumenkranz |
| 9,855,107 | B2 | 1/2018 | Labonville et al. |
| 9,872,737 | B2 | 1/2018 | Nixon |
| 9,877,718 | B2 | 1/2018 | Weir et al. |
| 9,883,920 | B2 | 2/2018 | Blumenkranz |
| 9,888,974 | B2 | 2/2018 | Niemeyer |
| 9,895,813 | B2 | 2/2018 | Blumenkranz et al. |
| 9,901,408 | B2 | 2/2018 | Larkin |
| 9,918,800 | B2 | 3/2018 | Itkowitz et al. |
| 9,943,375 | B2 | 4/2018 | Blumenkranz et al. |
| 9,948,852 | B2 | 4/2018 | Lilagan et al. |
| 9,949,798 | B2 | 4/2018 | Weir |
| 9,949,802 | B2 | 4/2018 | Cooper |
| 9,952,107 | B2 | 4/2018 | Blumenkranz et al. |
| 9,956,041 | B2 | 5/2018 | Zarrouk et al. |
| 9,956,044 | B2 | 5/2018 | Gomez et al. |
| 9,980,778 | B2 | 5/2018 | Ohline et al. |
| 10,008,017 | B2 | 6/2018 | Itkowitz et al. |
| 10,028,793 | B2 | 7/2018 | Griffiths et al. |
| 10,033,308 | B2 | 7/2018 | Chaghajerdi et al. |
| 10,034,719 | B2 | 7/2018 | Richmond et al. |
| 10,052,167 | B2 | 8/2018 | Au et al. |
| 10,085,811 | B2 | 10/2018 | Weir et al. |
| 10,092,165 | B2 | 10/2018 | Power |
| 10,092,344 | B2 | 10/2018 | Mohr et al. |
| 10,123,844 | B2 | 11/2018 | Nowlin |
| 10,188,471 | B2 | 1/2019 | Brisson |
| 10,201,390 | B2 | 2/2019 | Swarup et al. |
| 10,213,202 | B2 | 2/2019 | Flanagan et al. |
| 10,258,416 | B2 | 4/2019 | Mintz et al. |
| 10,278,782 | B2 | 5/2019 | Jarc et al. |
| 10,278,783 | B2 | 5/2019 | Itkowitz et al. |
| 10,282,881 | B2 | 5/2019 | Itkowitz et al. |
| 10,335,242 | B2 | 7/2019 | Devengenzo et al. |
| 10,350,130 | B2 | 7/2019 | Hughes et al. |
| 10,405,934 | B2 | 9/2019 | Prisco et al. |
| 10,433,922 | B2 | 10/2019 | Itkowitz et al. |
| 10,464,219 | B2 | 11/2019 | Robinson et al. |
| 10,485,621 | B2 | 11/2019 | Morrissette et al. |
| 10,500,004 | B2 | 12/2019 | Hanuschik et al. |
| 10,500,005 | B2 | 12/2019 | Weir et al. |
| 10,500,007 | B2 | 12/2019 | Richmond et al. |
| 10,507,066 | B2 | 12/2019 | DiMaio et al. |
| 10,510,267 | B2 | 12/2019 | Jarc et al. |
| 10,524,871 | B2 | 1/2020 | Liao |
| 10,548,459 | B2 | 2/2020 | Itkowitz et al. |
| 10,575,909 | B2 | 3/2020 | Robinson et al. |
| 10,592,529 | B2 | 3/2020 | Hoffman et al. |
| 10,595,946 | B2 | 3/2020 | Nixon |
| 10,881,469 | B2 | 1/2021 | Robinson |
| 10,881,473 | B2 | 1/2021 | Itkowitz et al. |
| 10,898,188 | B2 | 1/2021 | Burbank |
| 10,898,189 | B2 | 1/2021 | McDonald, II |
| 10,905,506 | B2 | 2/2021 | Itkowitz et al. |
| 10,912,544 | B2 | 2/2021 | Brisson et al. |
| 10,912,619 | B2 | 2/2021 | Jarc et al. |
| 10,918,387 | B2 | 2/2021 | Duque et al. |
| 10,918,449 | B2 | 2/2021 | Solomon et al. |
| 10,932,873 | B2 | 3/2021 | Griffiths et al. |
| 10,932,877 | B2 | 3/2021 | Devengenzo et al. |
| 10,939,969 | B2 | 3/2021 | Swarup et al. |
| 10,939,973 | B2 | 3/2021 | DiMaio et al. |
| 10,952,801 | B2 | 3/2021 | Miller et al. |
| 10,965,933 | B2 | 3/2021 | Jarc |
| 10,966,742 | B2 | 4/2021 | Rosa et al. |
| 10,973,517 | B2 | 4/2021 | Wixey |
| 10,973,519 | B2 | 4/2021 | Weir et al. |
| 10,984,567 | B2 | 4/2021 | Itkowitz et al. |
| 10,993,773 | B2 | 5/2021 | Cooper et al. |
| 10,993,775 | B2 | 5/2021 | Cooper et al. |
| 11,000,331 | B2 | 5/2021 | Krom et al. |
| 11,013,567 | B2 | 5/2021 | Wu et al. |
| 11,020,138 | B2 | 6/2021 | Ragosta |
| 11,020,191 | B2 | 6/2021 | Diolaiti et al. |
| 11,020,193 | B2 | 6/2021 | Wixey et al. |
| 11,026,755 | B2 | 6/2021 | Weir et al. |
| 11,026,759 | B2 | 6/2021 | Donlon et al. |
| 11,040,189 | B2 | 6/2021 | Vaders et al. |
| 11,045,077 | B2 | 6/2021 | Stern et al. |

(56) References Cited

U.S. PATENT DOCUMENTS

| | | | |
|---|---|---|---|
| 11,045,274 | B2 | 6/2021 | Dachs, II et al. |
| 11,058,501 | B2 | 7/2021 | Tokarchuk et al. |
| 11,076,925 | B2 | 8/2021 | DiMaio et al. |
| 11,090,119 | B2 | 8/2021 | Burbank |
| 11,096,687 | B2 | 8/2021 | Flanagan et al. |
| 11,098,803 | B2 | 8/2021 | Duque et al. |
| 11,109,925 | B2 | 9/2021 | Cooper et al. |
| 11,116,578 | B2 | 9/2021 | Hoffman et al. |
| 11,129,683 | B2 | 9/2021 | Steger et al. |
| 11,135,029 | B2 | 10/2021 | Suresh et al. |
| 11,147,552 | B2 | 10/2021 | Burbank et al. |
| 11,147,640 | B2 | 10/2021 | Jarc et al. |
| 11,154,373 | B2 | 10/2021 | Abbott et al. |
| 11,154,374 | B2 | 10/2021 | Hanuschik et al. |
| 11,160,622 | B2 | 11/2021 | Goldberg et al. |
| 11,160,625 | B2 | 11/2021 | Wixey et al. |
| 11,161,243 | B2 | 11/2021 | Rabindran et al. |
| 11,166,758 | B2 | 11/2021 | Mohr et al. |
| 11,166,770 | B2 | 11/2021 | DiMaio et al. |
| 11,166,773 | B2 | 11/2021 | Ragosta et al. |
| 11,173,597 | B2 | 11/2021 | Rabindran et al. |
| 11,185,378 | B2 | 11/2021 | Weir et al. |
| 11,191,596 | B2 | 12/2021 | Thompson et al. |
| 11,197,729 | B2 | 12/2021 | Thompson et al. |
| 11,213,360 | B2 | 1/2022 | Hourtash et al. |
| 11,221,863 | B2 | 1/2022 | Azizian et al. |
| 11,234,700 | B2 | 2/2022 | Ragosta et al. |
| 11,241,274 | B2 | 2/2022 | Vaders et al. |
| 11,241,290 | B2 | 2/2022 | Waterbury et al. |
| 11,259,870 | B2 | 3/2022 | DiMaio et al. |
| 11,259,884 | B2 | 3/2022 | Burbank |
| 11,272,993 | B2 | 3/2022 | Gomez et al. |
| 11,272,994 | B2 | 3/2022 | Saraliev et al. |
| 11,291,442 | B2 | 4/2022 | Wixey et al. |
| 11,291,513 | B2 | 4/2022 | Manzo et al. |
| 11,376,002 | B2 | 7/2022 | Shelton, IV et al. |
| 11,376,098 | B2 | 7/2022 | Shelton, IV et al. |
| 11,381,759 | B2 | 7/2022 | Zhao et al. |
| 11,382,621 | B2 | 7/2022 | Scheib et al. |
| 11,382,624 | B2 | 7/2022 | Harris et al. |
| 11,382,625 | B2 | 7/2022 | Huitema et al. |
| 11,382,626 | B2 | 7/2022 | Shelton, IV et al. |
| 11,382,627 | B2 | 7/2022 | Huitema et al. |
| 11,382,638 | B2 | 7/2022 | Harris et al. |
| 11,382,644 | B2 | 7/2022 | Schoettgen et al. |
| 11,389,160 | B2 | 7/2022 | Shelton, IV et al. |
| 11,389,255 | B2 | 7/2022 | DiMaio et al. |
| 11,399,906 | B2 | 8/2022 | Shelton, IV et al. |
| 11,406,379 | B2 | 8/2022 | Hess et al. |
| 11,410,259 | B2 | 8/2022 | Harris et al. |
| 11,419,630 | B2 | 8/2022 | Yates et al. |
| 11,424,027 | B2 | 8/2022 | Shelton, IV |
| 11,432,888 | B2 | 9/2022 | Diolaiti et al. |
| 11,432,893 | B2 | 9/2022 | Itkowitz et al. |
| 11,432,895 | B2 | 9/2022 | Loh et al. |
| 11,439,390 | B2 | 9/2022 | Patel et al. |
| 11,439,391 | B2 | 9/2022 | Bruns et al. |
| 11,468,791 | B2 | 10/2022 | Jarc et al. |
| 11,471,155 | B2 | 10/2022 | Shelton, IV et al. |
| 11,471,221 | B2 | 10/2022 | Zhao et al. |
| 11,478,308 | B2 | 10/2022 | Hoffman et al. |
| 11,490,977 | B2 | 11/2022 | Schena et al. |
| 11,497,499 | B2 | 11/2022 | Shelton, IV et al. |
| 11,504,119 | B2 | 11/2022 | Shelton, IV et al. |
| 11,504,124 | B2 | 11/2022 | Patel et al. |
| 11,510,743 | B2 | 11/2022 | Shelton, IV et al. |
| 11,517,312 | B2 | 12/2022 | Wixey |
| 11,517,325 | B2 | 12/2022 | Shelton, IV et al. |
| 11,518,048 | B2 | 12/2022 | Saraliev et al. |
| 2021/0322116 | A1* | 10/2021 | Swayze .................... B25J 9/102 |

FOREIGN PATENT DOCUMENTS

| | | |
|---|---|---|
| CN | 111496840 A | 8/2020 |
| WO | 2020208634 A1 | 10/2020 |
| WO | 2021201948 A2 | 10/2021 |
| WO | 2021234604 A1 | 11/2021 |

* cited by examiner

ROBOTIC SURGICAL ASSEMBLIES INCLUDING SURGICAL INSTRUMENTS HAVING ARTICULATABLE WRIST ASSEMBLIES

CROSS-REFERENCE TO RELATED APPLICATION

The present application claims priority to and the benefit of U.S. Patent Provisional Application No. 63/352,302, filed on Jun. 15, 2022. The entire contents of the foregoing application are incorporated by reference herein.

BACKGROUND

Some surgical robotic systems include a console supporting a surgical robotic arm and a surgical instrument or at least one end effector (e.g., forceps or a grasping tool) mounted to the robotic arm. The robotic arm provides mechanical power to the surgical instrument for its operation and movement. Each robotic arm may include an instrument drive unit operatively connected to the surgical instrument and coupled to the robotic arm via a rail. In operation, the robotic arm is moved to a position over a patient and then guides the surgical instrument into a small incision via a surgical trocar or a natural orifice of a patient to position the end effector at a work site within the patient's body. The instrument drive unit drives a rotation of each corresponding driven member of the attached surgical instrument to perform a surgical treatment. The instrument drive unit may be configured to articulate the end effector in a plurality of directions to adjust its pitch and/or yaw within a surgical site, to open/close jaw members, and/or to fire features thereof.

SUMMARY

In accordance with an aspect of the disclosure, a surgical instrument of a surgical robotic system is provided and includes a housing, a shaft extending distally from the housing, an end effector pivotably coupled to a distal end portion of the shaft, a first pair of first and second articulation cables, and a tensegrity wrist assembly. The articulation cables each have a proximal end portion operably coupled to an actuator, and a distal end portion secured to the end effector, such that the first pair of first and second articulation cables articulate the end effector relative to the shaft. The tensegrity wrist assembly includes a proximal coupler secured to the distal end portion of the shaft, a distal coupler secured to the end effector, and a link. The proximal coupler has an extension extending distally relative to the distal end portion of the shaft, and the distal coupler has an arm extending proximally relative to the end effector. The link is coupled to and extends between the extension of the proximal coupler and the arm of the distal coupler. The link is configured to apply opposing axial forces on the proximal and distal couplers.

In aspects, the extension of the proximal coupler may have a distal end secured to a distal end of the link, and the arm of the distal coupler may have a proximal end secured to a proximal end of the link.

In aspects, the distal end of the extension of the proximal coupler may be in overlapping alignment with and distal of the proximal end of the arm of the distal coupler.

In aspects, the distal end of the extension of the proximal coupler and the proximal end of the arm of the distal coupler may be positioned on a central longitudinal axis defined by the tensegrity wrist assembly.

In aspects, the distal end of the extension of the proximal coupler may be coaxial with and distal of the proximal end of the arm of the distal coupler.

In aspects, the link may be a rigid or flexible rod and/or may be positioned on a central longitudinal axis defined by the tensegrity wrist assembly.

In aspects, the proximal coupler may include a hub secured to the distal end portion of the shaft, and the extension. The extension may include first and second arms extending distally from the hub. The link may have a distal end secured to a distal end of each of the first and second arms of the extension. The distal end of the link may be prevented from moving proximally relative to the first and second arms of the proximal coupler.

In aspects, the distal coupler may include a hub secured to the end effector, and the arm. The arm may extend proximally from the hub of the distal coupler. The link may have a proximal end secured to a proximal end of the arm and may be from moving distally relative to the arm of the distal coupler.

In aspects, the hub of each of the proximal and distal couplers may define a first pair of first and second channels having the first pair of first and second articulation cables slidably positioned therein.

In aspects, the surgical instrument may include a second pair of first and second articulation cables. The hub of each of the proximal and distal couplers may define a second pair of first and second channels having the second pair of first and second articulation cables slidably positioned therein.

In accordance with further aspects of the disclosure, a surgical robotic system is provided that includes a surgical robotic arm, an instrument drive unit configured to be supported on the surgical robotic arm, and a surgical instrument configured to be coupled to and driven by the instrument drive unit. The surgical instrument includes a housing configured to be attached to the instrument drive unit, a shaft extending distally from the housing, an end effector movably coupled to a distal end portion of the shaft, a first pair of first and second articulation cables, and a tensegrity wrist assembly. The first pair of first and second articulation cables each have a proximal end portion operably coupled to an actuator of the instrument drive unit, and a distal end portion secured to the end effector, such that the first pair of first and second articulation cables articulate the end effector relative to the shaft. The tensegrity wrist assembly includes a proximal coupler secured to the distal end portion of the shaft, a distal coupler secured to the end effector, and a link. The proximal coupler has a pair of first and second arms extending distally relative to the distal end portion of the shaft. The distal coupler has an arm extending proximally relative to the end effector. The link includes a proximal end secured to a proximal end of the arm of the distal coupler, and a distal end secured to a distal end of each of the first and second arms of the proximal coupler. The link is configured to apply opposing axial forces on the proximal and distal couplers.

In aspects, the distal end of each of the first and second arms of the proximal coupler may be in overlapping alignment with and distal of the proximal end of the arm of the distal coupler.

In aspects, the distal end of each of the first and second arms of the proximal coupler may be coaxial with and distal of the proximal end of the arm of the distal coupler.

In aspects, the proximal coupler may include a hub defining a pair of channels having the first pair of first and second articulation cables slidably positioned therein. The first and second arms may extend distally from the hub. The distal coupler may include a hub defining a pair of channels having the first pair of first and second articulation cables slidably positioned therein. The arm extends proximally from the hub of the distal coupler.

In accordance with further aspects of the disclosure, a surgical instrument of a surgical robotic system is provided that includes a housing, a shaft extending distally from the housing, an end effector pivotably coupled to a distal end portion of the shaft, and a tensegrity wrist assembly. The tensegrity wrist assembly includes a proximal coupler, a distal coupler, and a link. The proximal coupler includes a hub secured to the distal end portion of the shaft, and an extension extending distally from the hub. The distal coupler includes a hub secured to the end effector, and an arm extending proximally from the hub of the distal coupler. The link includes a proximal end secured to a proximal end of the arm of the distal coupler, and a distal end secured to a distal end of the extension of the proximal coupler. The proximal end of the link is prevented from moving distally relative to the arm of the distal coupler and the distal end of the link is prevented from moving proximally relative to the extension of the proximal coupler such that the link is configured to maintain an axial separation between the proximal and distal couplers.

In aspects, the surgical instrument may further include a first pair of first and second articulation cables each including a distal end portion secured to the end effector, such that the first pair of first and second articulation cables articulate the end effector relative to the shaft.

In aspects, the hub of each of the proximal and distal couplers may define a first pair of first and second channels having the first pair of first and second articulation cables slidably positioned therein.

In aspects, the surgical instrument may further include a second pair of first and second articulation cables. The hub of each of the proximal and distal couplers may define a second pair of first and second channels having the second pair of first and second articulation cables slidably positioned therein.

Further details and aspects of exemplary embodiments of the disclosure are described in more detail below with reference to the appended figures.

As used herein, the terms parallel and perpendicular are understood to include relative configurations that are substantially parallel and substantially perpendicular up to about + or −10 degrees from true parallel and true perpendicular.

BRIEF DESCRIPTION OF THE DRAWINGS

Embodiments of the disclosure are described herein with reference to the accompanying drawings, wherein.

DETAILED DESCRIPTION

Figure 1:
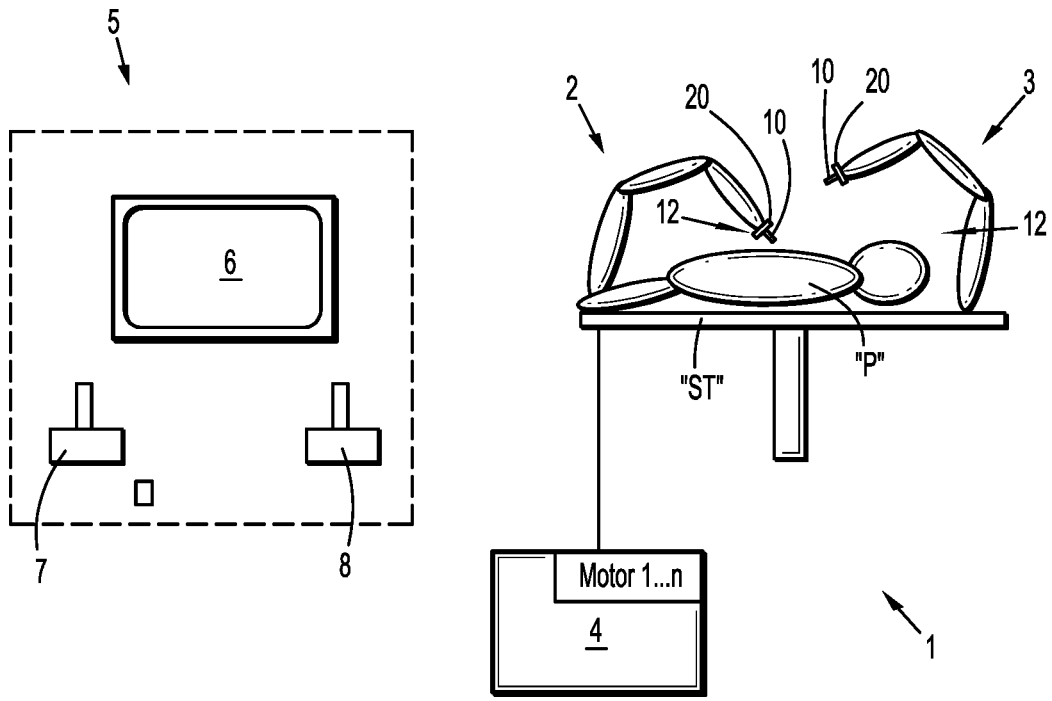
FIG. 1 is a schematic illustration of a robotic surgical system in accordance with the disclosure.

Embodiments of the disclosed robotic surgical system and methods thereof are described in detail with reference to the drawings, in which like reference numerals designate identical or corresponding elements in each of the several views. As used herein the term "distal" refers to that portion of the robotic surgical system or component thereof that is further from the user, while the term "proximal" refers to that portion of the robotic surgical system or component thereof that is closer to the user.

A robotically-controlled surgical instrument may include a wrist assembly that allows for articulation of an end effector in a plurality of directions to change, for example, a pitch or yaw of the end effector. However, the wrist assembly may be prone to wear and tear and may have dead space. Accordingly, this disclosure provides a wrist assembly that implements a tensegrity structure that allows for reduced resistance to articulation of the end effector, limits wear and tear on the wrist assembly, and maintains a spatial separation between the end effector and a distal end of a shaft.

Figure 2:
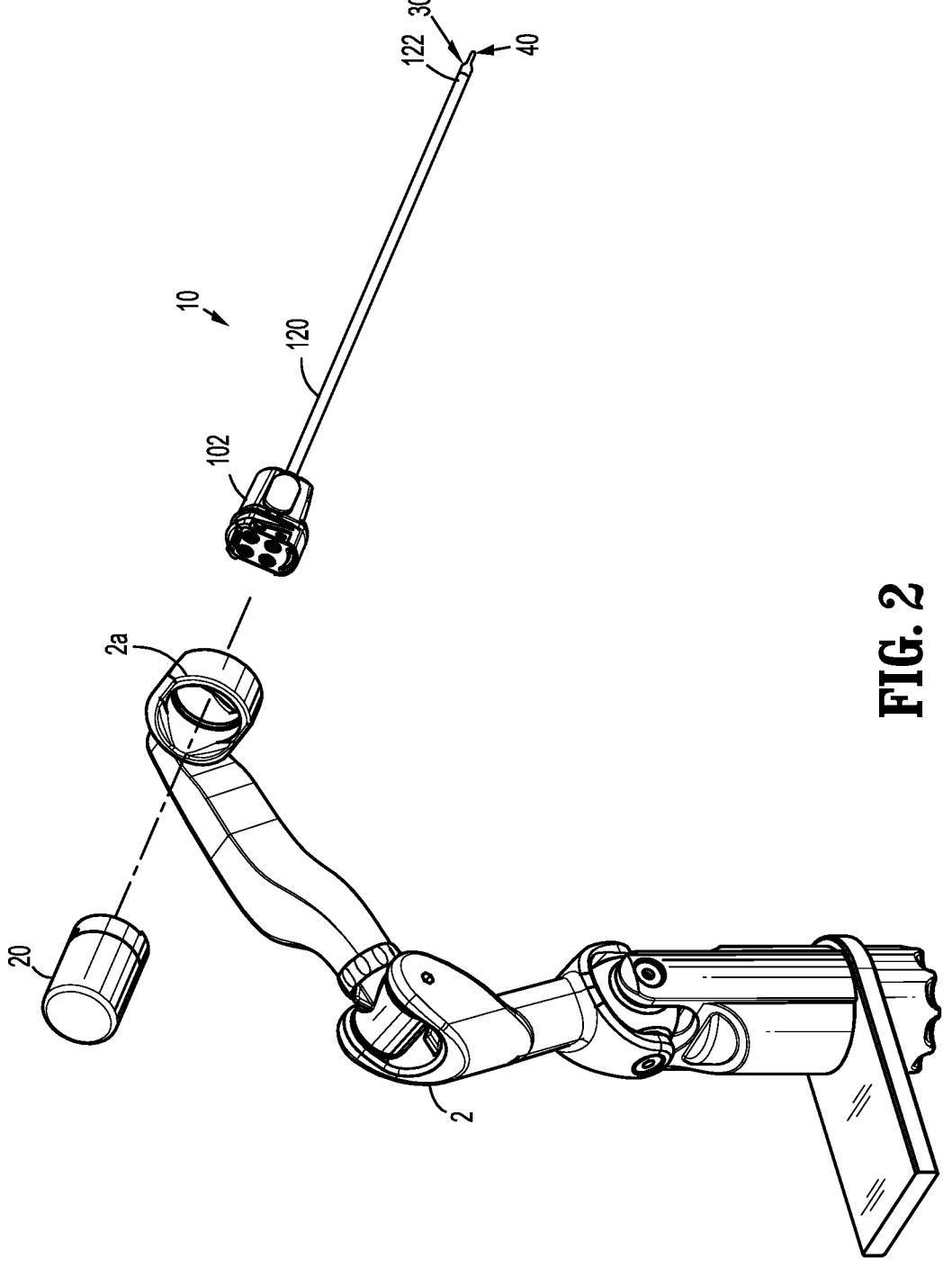
FIG. 2 is a perspective view of a surgical robotic arm of the robotic surgical system of FIG. 1 illustrating a surgical instrument and an instrument drive unit being coupled to the surgical robotic arm.
Figure 3:
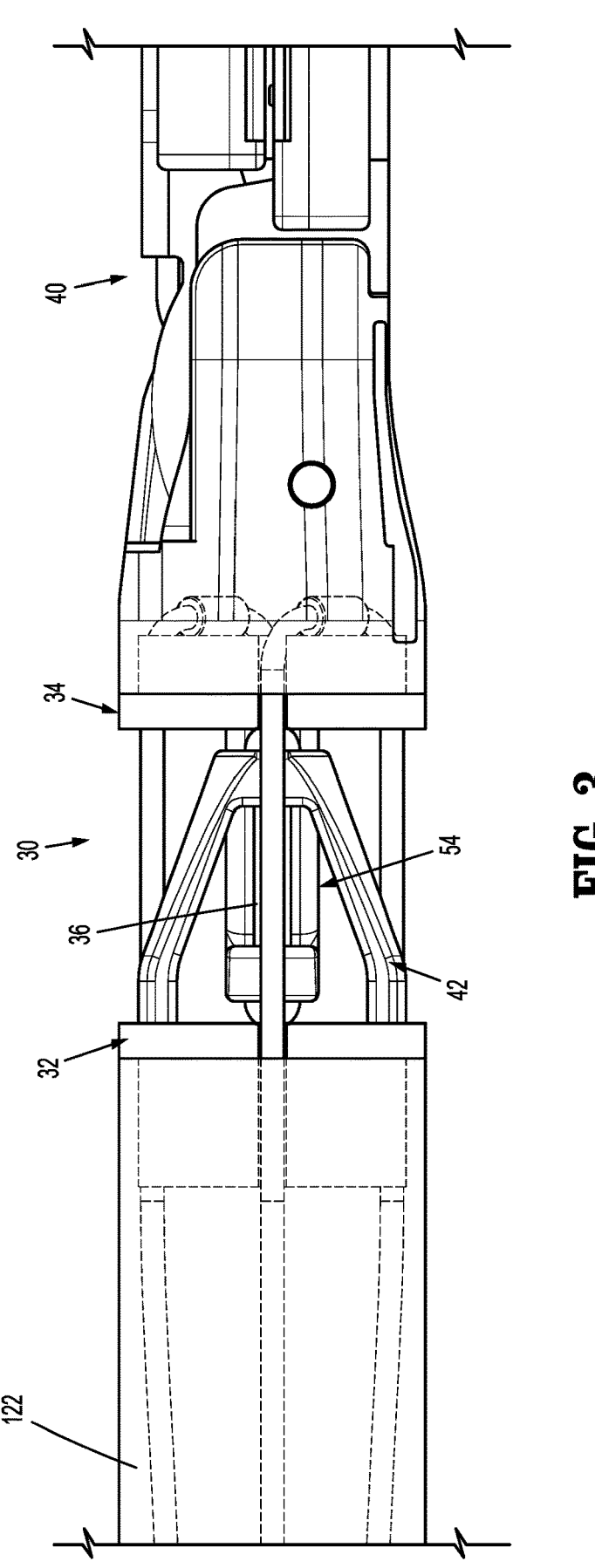
FIG. 3 is a side view illustrating a wrist assembly of the surgical instrument shown in FIG. 2 coupled between a shaft and an end effector of the surgical instrument.

Referring initially to FIGS. 1 and 2, a robotic surgical system 1 is shown and generally includes a plurality of surgical robotic arms 2, 3 each having a surgical instrument 10 (e.g., an electrosurgical instrument, a surgical stapling instrument, a surgical forceps, or the like) removably coupled thereto; a control device 4 (e.g., a computer); and an operating console 5 coupled with the control device 4.

With continued reference to FIG. 1, the operating console 5 includes a display device 6, which is set up to display two-dimensional and three-dimensional images; and manual input devices 7, 8 that serve to enable a user (e.g., a surgeon) to telemanipulate robotic arms 2, 3, as known in principle to a person skilled in the art. Each of the robotic arms 2, 3 may include a plurality of members that are interconnected by joints. The robotic arms 2, 3 may be driven by electric drives (not shown) that are connected to the control device 4. The control device 4 is set up to execute a computer program to activate the electric drives in such a way that the robotic arms 2, 3, their instrument drive units 20, and thus the surgical instrument 10 execute a movement in accordance with a movement of the manual input devices 7, 8. The control device 4 may also be set up in such a way that it regulates the movement of the robotic arms 2, 3 and/or of the electric drives.

The robotic surgical system 1 is configured for minimally invasive treatment of a patient "P" lying on a surgical table "ST" using a surgical instrument (e.g., surgical instrument 10) coupled to the robotic surgical system 1. In some embodiments of the disclosure, the robotic surgical system 1 may include more than two robotic arms that are likewise coupled to the control device 4 and telemanipulatable by the operating console 5. A surgical instrument (e.g., surgical instrument 10) may also be attached to the additional robotic arm(s).

The surgical instrument 10 includes an end effector 40 (FIG. 2) for grasping and, in aspects, treating tissue. The control device 4 may control a plurality of motors (Motor 1 . . . n) with each motor configured to drive a relative rotation of drive members of a transmission assembly (not labeled) of the surgical instrument 10 to effect operation and/or movement of the end effector 40 of the surgical instrument 10. It is contemplated that the control device 4 coordinates the activation of the various motors (Motor 1 . . . n) to coordinate a clockwise or counterclockwise rotation of drive members (not shown) of the instrument drive unit 20 in order to coordinate an operation and/or movement of the end effector 40. In embodiments, each motor can be configured to actuate a drive rod or a lever arm to effect operation and/or movement of the end effector 40 of the surgical instrument 10.

With specific reference to FIG. 2, the robotic surgical system 1 includes a surgical assembly 12, which includes the robotic arm 2, the surgical instrument 10 coupled to the robotic arm 2, and the instrument drive unit 20 configured to operably couple to the surgical instrument 10. The instrument drive unit 20 is configured for powering the surgical instrument 10. The instrument drive unit 20 transfers power and actuation forces from its motors (not shown) to the transmission assembly of the surgical instrument 10 to ultimately drive movement of components of the end effector 40, for example, a movement of a knife blade (not explicitly shown) for cutting tissue and a closing and opening of jaw members of the end effector 40 for grasping tissue, and/or drive an articulation of the end effector 40.

The surgical instrument 10 generally includes a housing 102, a shaft 120 extending distally from the housing 102, and a tensegrity wrist assembly 30 pivotably coupling the end effector 40 to the shaft 120. The housing 102 is configured to hook, latch, or otherwise attach to a surface of the robotic arm 2, e.g., the distal end 2a of the robotic arm 2, to secure the surgical instrument 10 to the robotic arm 2. In embodiments, the housing 102 may be attached to the surgical robotic arm 2 via various fastening engagements, such as, for example, clips, latches, friction fit engagement, buttons, a variety of fasteners, and/or a bayonet-type connection. The housing 102 houses the transmission assembly that interfaces with the instrument drive unit 20. The transmission assembly translates the motion and torques of the motors of the instrument drive unit 20 into the motion necessary to articulate the wrist assembly 30 of the surgical instrument 10, open and close the jaw members of the end effector 40, and deploy and retract a knife blade to cut tissue grasped between the jaw members of the end effector 40.

With reference to FIGS. 3-7, the tensegrity wrist assembly 30 of the surgical instrument 10 operably couples the end effector 40 to a distal end portion 122 of the shaft 120. The tensegrity wrist assembly 30 generally includes a proximal body or coupler 32 immovably attached to the distal end portion 122 of the shaft 120, a distal body or coupler 34 immovably attached to a proximal end portion of the end effector 40, and a link 36 coupling the proximal and distal couplers 32, 34 to one another. The wrist assembly 30 is configured to affect the pivoting motion of the end effector 40 relative to the shaft 120 to adjust the yaw and/or pitch of the end effector 40 utilizing a series of translatable cables "C1," "C2," "C3," "C4" driven by the motors of the instrument drive unit 20. The articulation cables "C1," "C2," "C3," "C4" are routed through the wrist assembly 30 and fixed to the distal coupler 34 of the wrist assembly 30 or a proximal end of the end effector 40 for adjusting a pitch and yaw of the end effector 40.

Figure 7:
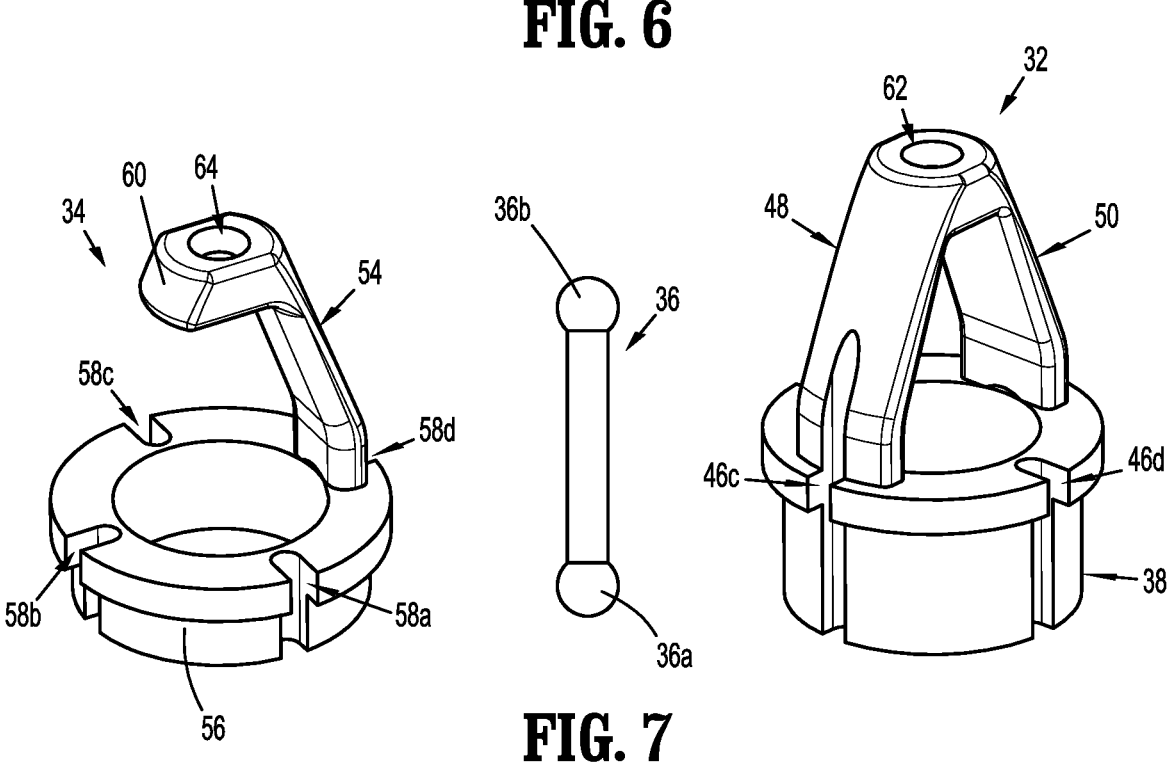
FIG. 7 is a perspective view, with parts separated, of the components of the wrist assembly of FIG. 4.

The proximal coupler 32 of the tensegrity wrist assembly 30 includes a hub 38 secured to the distal end portion 122 of the shaft 120, and an extension 42 extending distally from an outer circumference 44 of the hub 38. The outer circumference 44 of the hub 38 defines a first pair of opposed first and second channels 46a, 46b, and a second pair of first and second channels 46c, 46d (FIG. 7). The first pair of first and second articulation cables "C1," "C2" are slidably positioned in the first pair of first and second channels 46a, 46b, and the second pair of first and second articulation cables "C3," "C4" are slidably positioned in the second pair of first and second channels 46c, 46d.

Figure 5A:
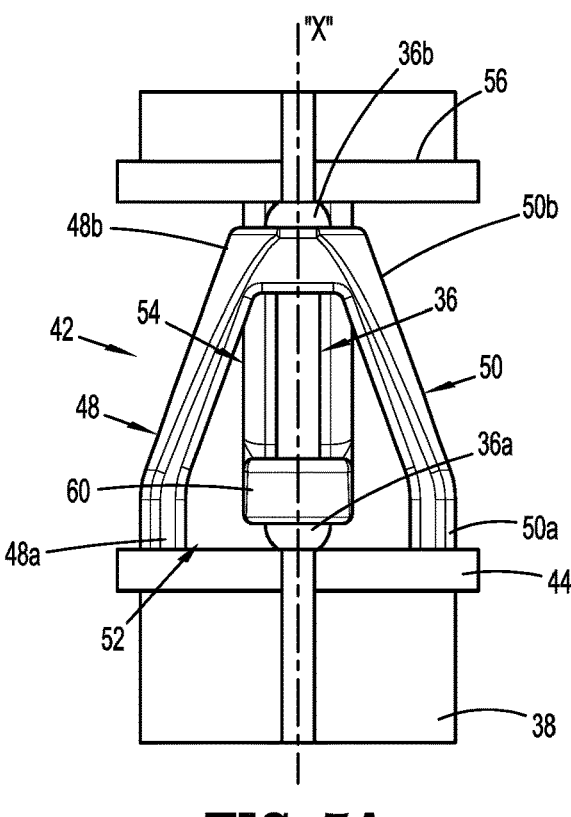
FIG. 5A is a side view illustrating components of the wrist assembly of FIG. 4.
Figure 5B:
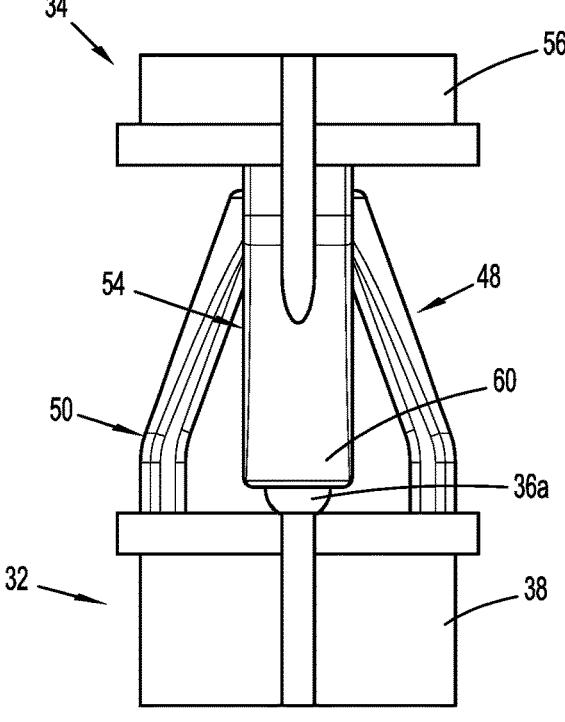
FIG. 5B is another side view illustrating the components of the wrist assembly of FIG. 4.
Figure 6:
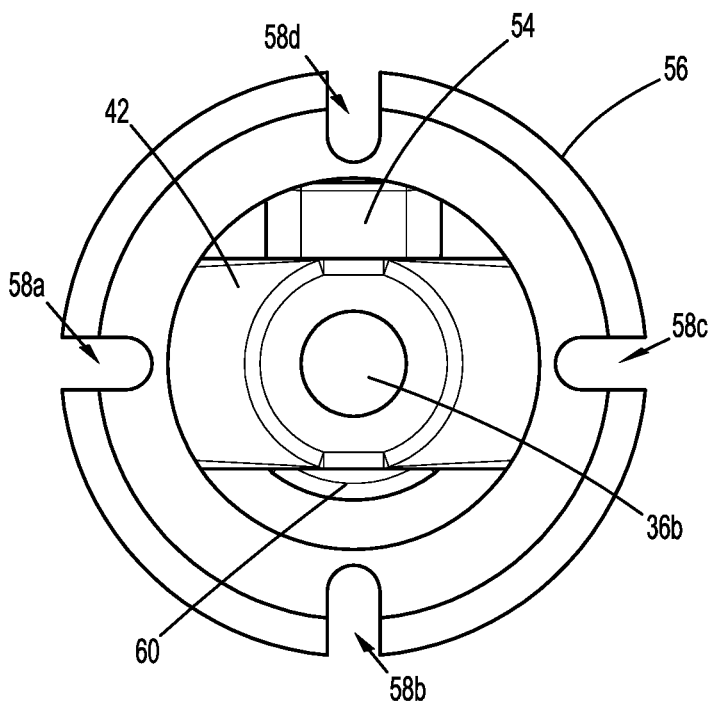
FIG. 6 is a top view illustrating the components of the wrist assembly of FIG. 4.

With reference to FIGS. 5A, 5B, and 7, the extension 42 of the proximal coupler 32 includes first and second arms 48, 50 extending distally from the hub 38. More specifically, the first and second arms 48, 50 each have a proximal end 48a, 50a secured to diametrically opposed portions of the outer circumference 44 of the hub 38, and a distal end 48b, 50b disposed radially inward of the outer circumference 44 of the hub 38. In a distal direction, the first and second arms 48, 50 may taper radially inward. The first and second arms 48, 50 define a space 52 therebetween having received therein an arm 54 of the distal coupler 34 of the wrist assembly 30. While the wrist assembly 30 is shown and described as having a first and second arms 48, 50, it is envisioned and contemplated that the first and second arms 48, 50 may be replaced by a single arm, or the like, without departing from the scope of the disclosure.

With reference to FIGS. 4-7, the distal coupler 34 of the wrist assembly 30 includes a hub 56 secured to the end effector 40, and the arm 54, which extends proximally from the hub 56 of the distal coupler 34. The hub 56 of the distal coupler 34 defines a first pair of first and second channels 58a, 58b having the first pair of first and second articulation cables "C1," "C2" slidably positioned therein, and a second pair of first and second channels 58c, 58d having the second pair of first and second articulation cables "C3," "C4" slidably positioned therein. The arm 54 of the distal coupler 34 has a proximal end 60 in overlapping alignment (e.g., coaxial) with the distal end 48b, 50b of each of the first and second arms 48, 50 of the proximal coupler 32. The distal end 48b, 50b of the first and second arms 48, 50 of the proximal coupler 32 and the proximal end 60 of the arm 54 of the distal coupler 34 are positioned on a central longitudinal axis "X" (FIG. 5A) defined by the tensegrity wrist assembly 30. While the wrist assembly 30 is shown and described as having a single arm 54, it is envisioned and contemplated that arm 54 may be replaced by a pair of arms, or the like, without departing from the scope of the disclosure.

The link 36 may be a rigid or flexible cable, rod, tether, tendon, or the like and is coupled to and extends between the extension 42 of the proximal coupler 32 and the arm 54 of the distal coupler 34. The link 36 is positioned on the central longitudinal axis "X" of the wrist assembly 30 and radially inward of each of the articulation cables "C1," "C2," "C3," "C4." The link 36 is configured to apply opposing tension forces on the proximal and distal couplers 32, 34 to maintain an axial separation between the end effector 40 and the distal end portion 122 of the shaft 120. The link 36 and the articulation cables "C1," "C2," "C3," "C4" may be the only mechanical couplings between the end effector 40 and the shaft 120.

The link 36 includes a distal end 36*b* secured to the distal end 48*b*, 50*b* of each of the first and second arms 48, 50 of the proximal coupler 32, and a proximal end 36*a* secured to the proximal end 60 of the arm 54 of the distal coupler 34. The distal end 36*b* of the link 36 may be bulbous or otherwise enlarged relative to a body of the link 36 and is positioned distally of an opening 62 (FIG. 7) defined in the distal end 48*b*, 50*b* of the first and second arms 48, 50 to prevent the distal end 36*b* of the link 36 from moving proximally relative to the first and second arms 48, 50 of the proximal coupler 32. The proximal end 36*a* of the link 36 may be bulbous or otherwise enlarged relative to the body of the link 36 and is positioned proximally of an opening 64 (FIG. 7) defined in the proximal end 60 of the arm 54 of the distal coupler 34 such that the proximal end 36*a* of the link 36 is prevented from moving distally relative to the arm 54 of the distal coupler 34. The proximal and distal ends 36*a*, 36*b* of the link 36 may be secured to the respective arm 54 of the distal coupler 34 and the extension 42 of the proximal coupler 32 in other suitable fastening engagements, such as, for example, adhesives, friction fit, or fasteners.

Figure 4:
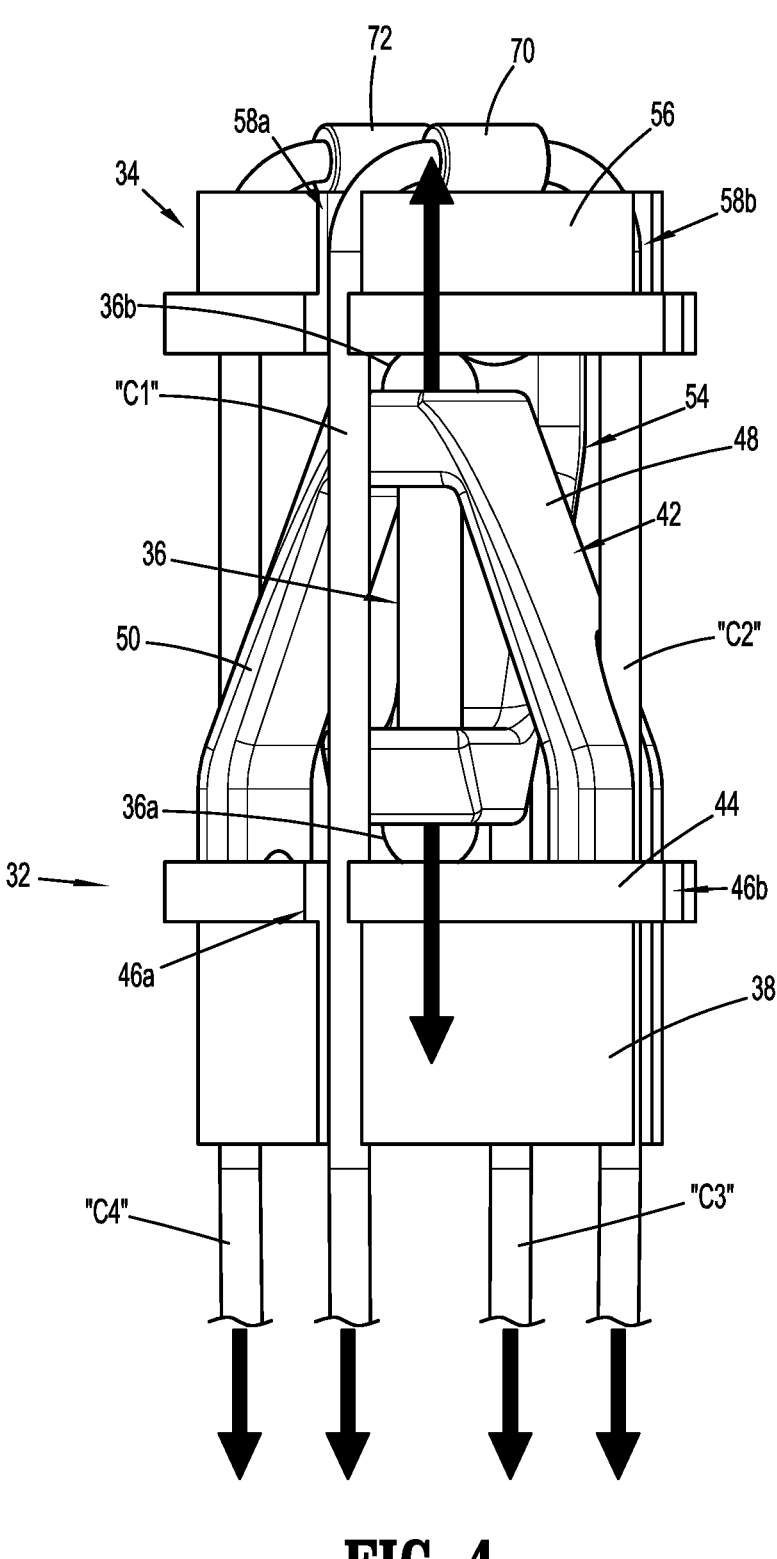
FIG. 4 is a side view illustrating components of the wrist assembly of FIG. 3.
Figure 8A:
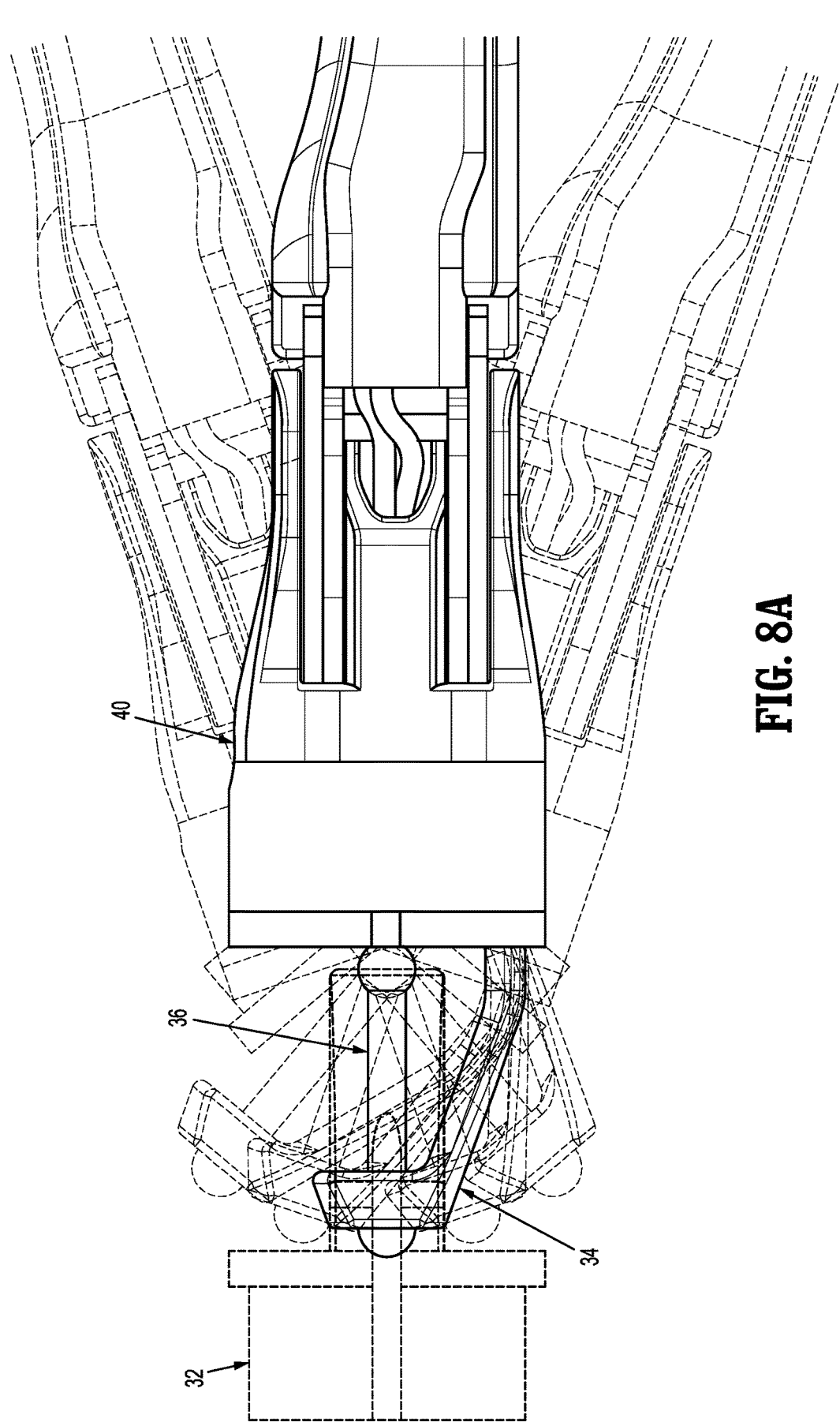
FIG. 8A is a side view illustrating a first plurality of articulation orientations of the end effector of the surgical instrument.
Figure 8B:
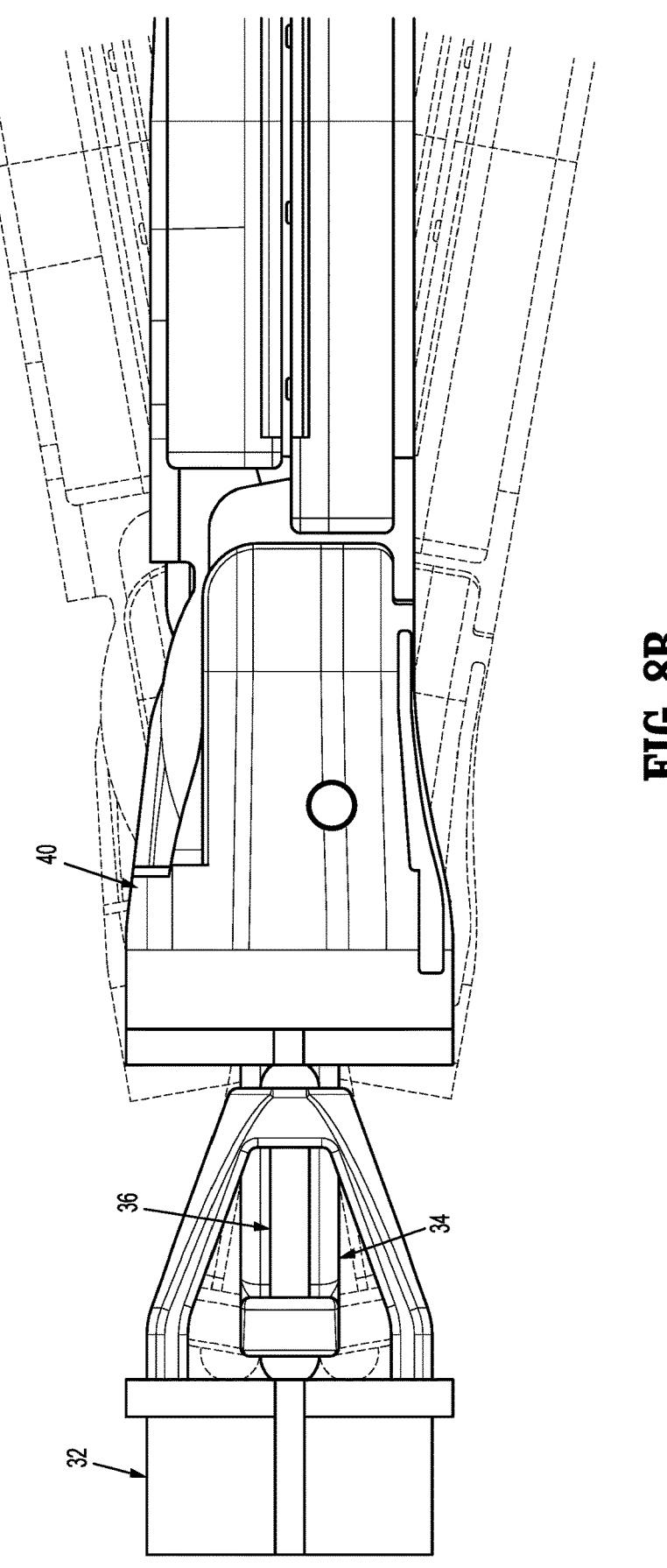
FIG. 8B is another side view illustrating a second plurality of articulation orientations of the end effector of the surgical instrument.

With reference to FIGS. 4, 8A, and 8B, the first and second articulation cables "C1," "C2" each have a proximal end portion (not explicitly shown) operably coupled to an actuator or actuators (not explicitly shown) of the instrument drive unit 20 (FIG. 2), and a distal end portion secured to the end effector 40. The articulation cables "C3," "C4" each have a proximal end portion (not explicitly shown) operably coupled to an actuator or actuators (not explicitly shown) of the instrument drive unit 20, and a distal end portion 72 secured to the end effector 40. As shown in FIG. 8A, the articulation cables "C1," "C2," "C3," "C4" work together to articulate the end effector 40 relative to the shaft 120 to adjust a pitch and/or a yaw of the end effector 40. For example, to adjust the pitch and/or yaw of the end effector 40, and thus to articulate the end effector 40, cable "C1" (and possibly cables "C3" and/or "C4") may be translated proximally and cable "C2" (and possibly cables "C3" and/or "C4") may be translated distally. As shown in FIG. 8B, the articulation cables "C1," "C2," "C3," "C4" work together to articulate the end effector 40 relative to the shaft 120 to adjust a pitch and/or a yaw of the end effector 40. For example, to adjust the yaw of the end effector 40, cable "C4" may be translated proximally and cable "C3" may be translated distally. The articulation cables "C1," "C2," "C3," "C4" are held in tension to prevent the distal coupler 34 and the proximal coupler 32 from axially separating while the tension in the link 36 of the wrist assembly 30 prevents the distal coupler 34 and the proximal coupler 34 from axially contracting.

It will be understood that various modifications may be made to the embodiments disclosed herein. Therefore, the above description should not be construed as limiting, but merely as exemplifications of various embodiments. Those skilled in the art will envision other modifications within the scope and spirit of the claims appended thereto.

The invention claimed is:

1. A surgical instrument of a surgical robotic system, the surgical instrument comprising:
 a housing;
 a shaft extending distally from the housing, the shaft having a distal end portion;
 a tensegrity wrist assembly including:
  a proximal coupler secured to the distal end portion of the shaft and having an extension extending distally relative to the distal end portion of the shaft;

a distal coupler secured to the end effector and having an arm extending proximally relative to the end effector; and
  a link coupled to and extending between the extension of the proximal coupler and the arm of the distal coupler, wherein the link is configured to apply opposing axial forces on the proximal and distal couplers;
 an end effector pivotably coupled to a distal end of the distal coupler of the tensegrity wrist assembly; and
 a first pair of first and second articulation cables each having a proximal end portion operably coupled to an actuator, and a distal end portion secured to the end effector, such that the first pair of first and second articulation cables articulate the end effector relative to the shaft.

2. The surgical instrument according to claim 1, wherein the extension of the proximal coupler has a distal end secured to a distal end of the link, and the arm of the distal coupler has a proximal end secured to a proximal end of the link.

3. The surgical instrument according to claim 2, wherein the distal end of the extension of the proximal coupler is in overlapping alignment with and distal of the proximal end of the arm of the distal coupler.

4. The surgical instrument according to claim 3, wherein the distal end of the extension of the proximal coupler and the proximal end of the arm of the distal coupler are positioned on a central longitudinal axis defined by the tensegrity wrist assembly.

5. The surgical instrument according to claim 2, wherein the distal end of the extension of the proximal coupler is coaxial with and distal of the proximal end of the arm of the distal coupler.

6. The surgical instrument according to claim 1, wherein the link is a rigid or flexible rod defining a link longitudinal axis, wherein the link longitudinal axis extends in a proximal to distal direction and is positioned on a central longitudinal axis defined by the tensegrity wrist assembly.

7. The surgical instrument according to claim 1, wherein the proximal coupler includes:
 a hub secured to the distal end portion of the shaft; and
 the extension, the extension including first and second arms extending distally from the hub, the link having a distal end secured to a distal end of each of the first and second arms of the extension and prevented from moving proximally relative to the first and second arms of the proximal coupler.

8. The surgical instrument according to claim 7, wherein the distal coupler includes:
 a hub secured to the end effector; and
 the arm, the arm extending proximally from the hub of the distal coupler, the link having a proximal end secured to a proximal end of the arm and prevented from moving distally relative to the arm of the distal coupler.

9. The surgical instrument according to claim 8, wherein the hub of each of the proximal and distal couplers defines a first pair of first and second channels having the first pair of first and second articulation cables slidably positioned therein.

10. The surgical instrument according to claim 9, further comprising a second pair of first and second articulation cables, wherein the hub of each of the proximal and distal couplers defines a second pair of first and second channels having the second pair of first and second articulation cables slidably positioned therein.

11. A surgical robotic system, comprising:

a surgical robotic arm;

an instrument drive unit configured to be supported on the surgical robotic arm; and a surgical instrument configured to be coupled to and driven by the instrument drive unit, the surgical instrument including;

a housing configured to be attached to the instrument drive unit;

a shaft extending distally from the housing, the shaft having a distal end portion;

a tensegrity wrist assembly including:

a proximal coupler secured to the distal end portion of the shaft and having a pair of first and second arms extending distally relative to the distal end portion of the shaft;

a distal coupler secured to the end effector and having an arm extending proximally relative to the end effector; and a link including a proximal end secured to a proximal end of the arm of the distal coupler, and a distal end secured to a distal end of each of the first and second arms of the proximal coupler, wherein the link is configured to apply opposing axial forces on the proximal and distal couplers;

an end effector pivotably coupled to a distal end of the distal coupler of the tensegrity wrist assembly; and a first pair of first and second articulation cables each having a proximal end portion operably coupled to an actuator of the instrument drive unit, and a distal end portion secured to the end effector, such that the first pair of first and second articulation cables articulate the end effector relative to the shaft.

12. The surgical robotic system according to claim 11, wherein the distal end of each of the first and second arms of the proximal coupler is in overlapping alignment with and distal of the proximal end of the arm of the distal coupler.

13. The surgical robotic system according to claim 11, wherein the distal end of each of the first and second arms of the proximal coupler is coaxial with and distal of the proximal end of the arm of the distal coupler.

14. The surgical robotic system according to claim 11, wherein the link is a rigid or flexible rod defining a link longitudinal axis, wherein the link longitudinal axis extends in a proximal to distal direction and is positioned on a central longitudinal axis defined by the tensegrity wrist assembly.

15. The surgical robotic system according to claim 11, wherein the proximal coupler includes a hub defining a pair of channels having the first pair of first and second articulation cables slidably positioned therein, the first and second arms extending distally from the hub, wherein the distal coupler includes a hub defining a pair of channels having the first pair of first and second articulation cables slidably positioned therein, the arm extending proximally from the hub of the distal coupler.

16. A surgical instrument of a surgical robotic system, the surgical instrument comprising:

a housing;

a shaft extending distally from the housing, the shaft having a distal end portion;

a tensegrity wrist assembly including:

a proximal coupler including:

a hub secured to the distal end portion of the shaft; and an extension extending distally from the hub;

a distal coupler including:

a hub secured to the end effector; and an arm extending proximally from the hub of the distal coupler; and a link defining a link longitudinal axis, wherein the link longitudinal axis extends in a proximal to distal direction, the link including a proximal end secured to a proximal end of the arm of the distal coupler, and a distal end secured to a distal end of the extension of the proximal coupler, the proximal end of the link being prevented from moving distally relative to the arm of the distal coupler and the distal end of the link being prevented from moving proximally relative to the extension of the proximal coupler such that the link is configured to maintain an axial separation between the proximal and distal couplers; and an end effector pivotably coupled to a distal end of the distal coupler of the tensegrity wrist assembly.

17. The surgical instrument according to claim 16, wherein the distal end of the extension of the proximal coupler is in overlapping alignment with and distal of the proximal end of the arm of the distal coupler.

18. The surgical instrument according to claim 16, further comprising a first pair of first and second articulation cables each including a distal end portion secured to the end effector, such that the first pair of first and second articulation cables articulate the end effector relative to the shaft.

19. The surgical instrument according to claim 18, wherein the hub of each of the proximal and distal couplers defines a first pair of first and second channels having the first pair of first and second articulation cables slidably positioned therein.

20. The surgical instrument according to claim 19, further comprising a second pair of first and second articulation cables, wherein the hub of each of the proximal and distal couplers defines a second pair of first and second channels having the second pair of first and second articulation cables slidably positioned therein.

* * * * *